(12) United States Patent
Hazaki et al.

(10) Patent No.: US 7,553,334 B2
(45) Date of Patent: Jun. 30, 2009

(54) DEFECTIVE PRODUCT INSPECTION APPARATUS, PROBE POSITIONING METHOD AND PROBE MOVING METHOD

(75) Inventors: Eiichi Hazaki, Tsuchiura (JP); Yasuhiro Mitsui, Fuchu (JP); Takashi Furukawa, Sagamihara (JP); Hiroshi Yanagita, Koganei (JP); Susumu Kato, Hitachinaka (JP); Osamu Satou, Hitachinaka (JP); Osamu Yamada, Hitachinaka (JP); Yoshikazu Inada, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/976,238

(22) Filed: Oct. 23, 2007

(65) Prior Publication Data
US 2008/0048699 A1 Feb. 28, 2008

Related U.S. Application Data

(63) Continuation of application No. 11/002,710, filed on Dec. 3, 2004, now Pat. No. 7,297,945.

(30) Foreign Application Priority Data
Dec. 5, 2003 (JP) .............................. 2003-406707

(51) Int. Cl.
*G01N 13/10* (2006.01)
(52) U.S. Cl. .............................. 850/8; 850/9; 250/306; 250/310
(58) Field of Classification Search .................. 250/306; 324/758
See application file for complete search history.

(56) References Cited

U.S. PATENT DOCUMENTS

| | | | | |
|---|---|---|---|---|
| 4,532,423 A | * | 7/1985 | Tojo et al. .................... | 250/310 |
| 5,349,735 A | * | 9/1994 | Kawase et al. ........... | 29/407.05 |

(Continued)

FOREIGN PATENT DOCUMENTS

JP    9-26436    1/1997

(Continued)

OTHER PUBLICATIONS

German Office Action issued in Patent Application No. 10 2004 058 483.4-35 dated on Jul. 31, 2008.

*Primary Examiner*—David A. Vanore
(74) *Attorney, Agent, or Firm*—McDermott Will & Emery LLP

(57) ABSTRACT

For adjusting a positional relationship between a specimen and a probe to measure an electric characteristic of the specimen through a contact therebetween, a base table holding a specimen table holding the specimen and a probe holder holding the probe is positioned at a first position to measure the positional relationship between the probe and the specimen at the first position, and subsequently positioned at a second position to measure the positional relationship therebetween at the second position so that the probe and the specimen are contact each other at the second position, the specimen table and the probe holder are movable with respect to each other on the base table at each of the first and second positions to adjust the positional relationship between the probe and the specimen, and a measuring accuracy at the second position is superior to a measuring accuracy at the first position.

9 Claims, 12 Drawing Sheets

U.S. PATENT DOCUMENTS

| | | | | |
|---|---|---|---|---|
| 5,675,499 | A * | 10/1997 | Lee et al. | 716/19 |
| 6,096,567 | A | 8/2000 | Kaplan et al. | |
| 6,191,598 | B1 | 2/2001 | Hollman | |
| 6,198,299 | B1 * | 3/2001 | Hollman | 324/758 |
| 6,420,825 | B1 * | 7/2002 | Shinjo et al. | 313/495 |
| 6,610,257 | B2 * | 8/2003 | Vane | 422/186.04 |
| 6,621,282 | B2 * | 9/2003 | Hollman | 324/758 |
| 6,683,316 | B2 * | 1/2004 | Schamber et al. | 250/492.1 |
| 6,744,268 | B2 * | 6/2004 | Hollman | 324/758 |
| 6,838,895 | B2 * | 1/2005 | Hollman | 324/758 |
| 6,861,648 | B2 * | 3/2005 | Kley | 250/306 |
| 7,043,848 | B2 * | 5/2006 | Hollman et al. | 33/556 |
| 7,180,317 | B2 * | 2/2007 | Hollman | 324/760 |
| 7,297,945 | B2 * | 11/2007 | Hazaki et al. | 250/306 |
| 2002/0000819 | A1 * | 1/2002 | Hollman | 324/758 |
| 2003/0042921 | A1 | 3/2003 | Hollman | |
| 2004/0056672 | A1 | 3/2004 | Hollman | |

FOREIGN PATENT DOCUMENTS

| | | |
|---|---|---|
| JP | 9-326425 | 12/1997 |
| JP | 2000-147070 | 5/2000 |
| JP | 2002-181898 | 6/2002 |
| JP | 2002-523784 | 7/2002 |
| JP | 2003-309153 | 10/2003 |

* cited by examiner

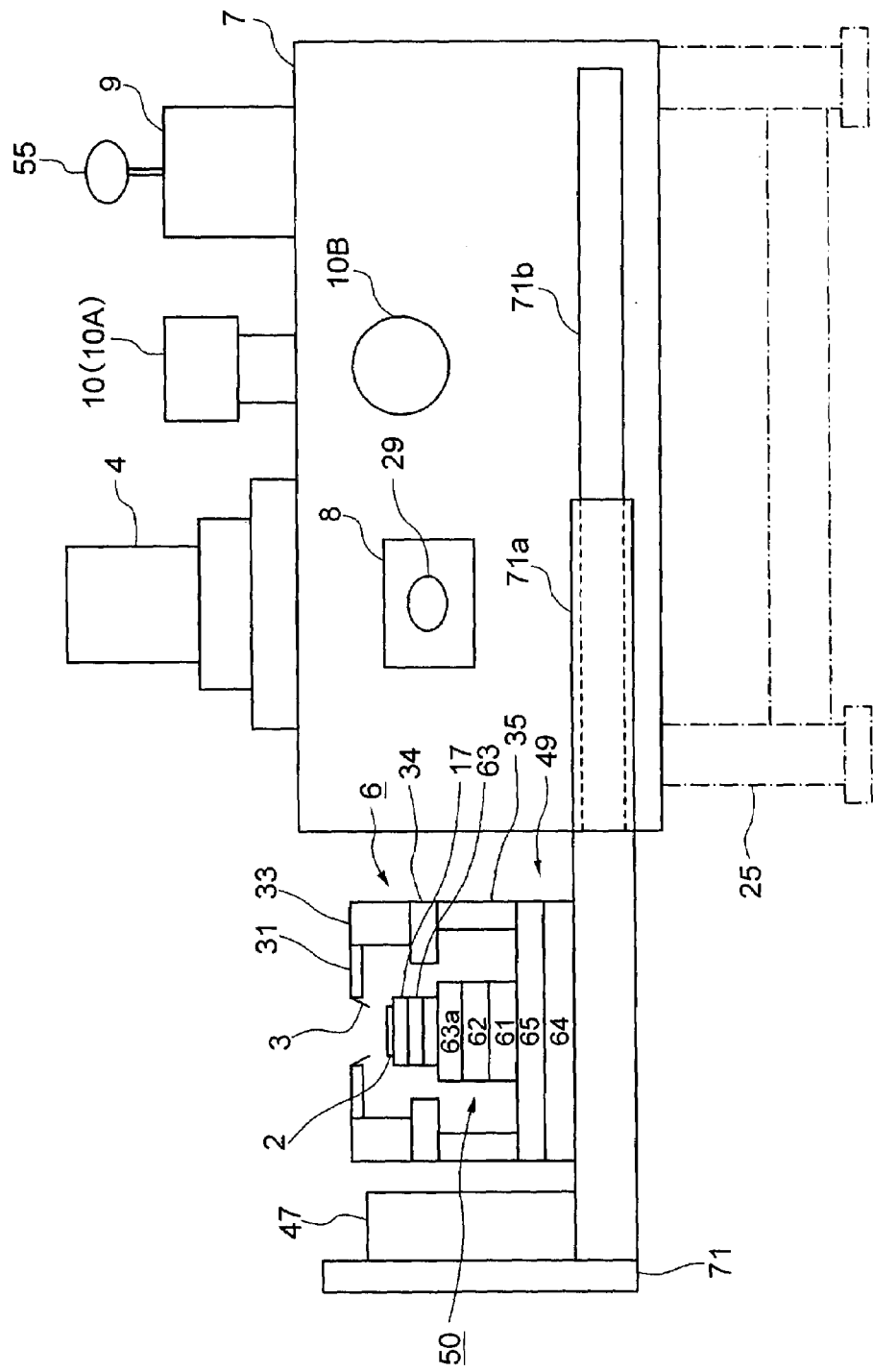

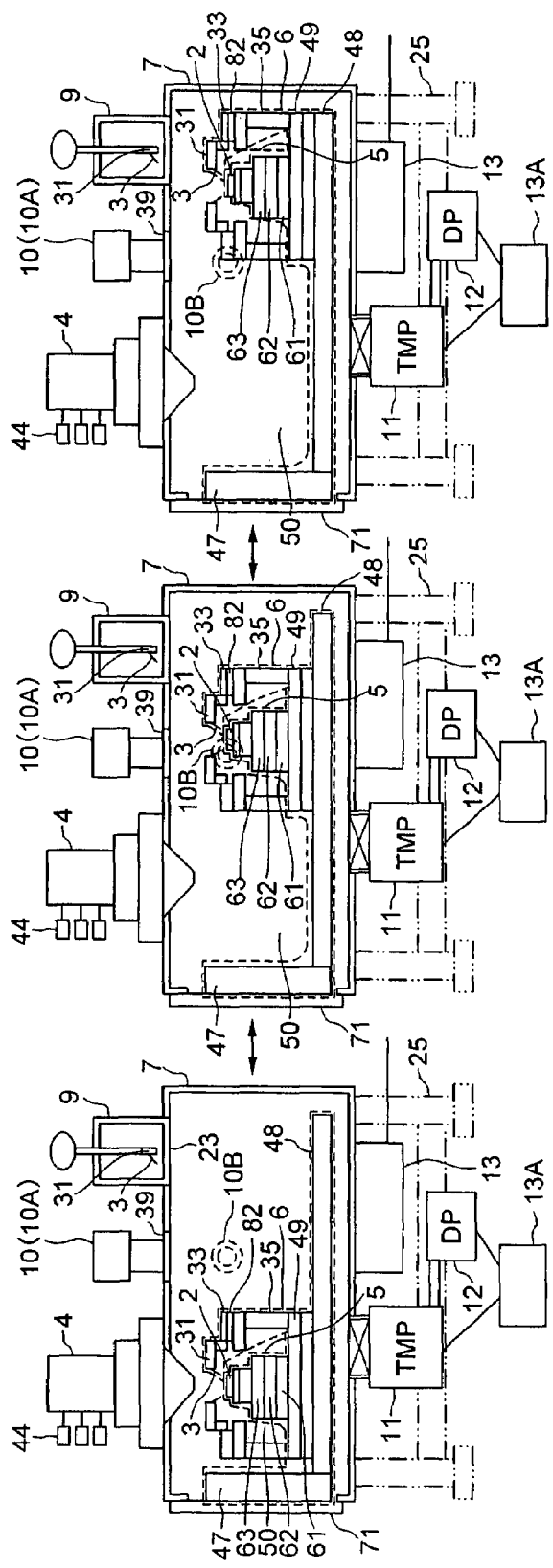

DEFECTIVE PRODUCT INSPECTION APPARATUS, PROBE POSITIONING METHOD AND PROBE MOVING METHOD

This application is a Continuation of U.S. application Ser. No. 11/002,710, filed Dec. 3, 2004 now U.S. Pat. No. 7,297,945, claiming priority of Japanese Application No. 2003-406707, filed Dec. 5, 2003, the entire contents of each of which are hereby incorporated by reference.

BACKGROUND OF THE INVENTION

The present invention relates to a defective product inspection apparatus (probe apparatus), a probe positioning method and a probe moving method, for measuring an electric characteristic of a microscopic area of an electronic element.

A defective product inspection apparatus is well known as the prior art, in which a probe contacts an area of a specimen (an electronic element) at which an electric characteristic needs to be inspected. An electric current-voltage characteristic or the like of the electronic element can be measured through the probe.

JP-A-9-326425 discloses that a probe is arranged in a specimen chamber of a scanning electron microscope (SEM) to measure a minute electric potential characteristic.

JP-A-2000-147070 discloses a probe apparatus in which a probe information image showing an information for operating desirably a probe is formed on a display, a specimen and the probe are shown in the probe information image on the display, a probe operating image area for moving the probe is formed on the display, the probe is moved through a probe controller in accordance with an operating signal from the probe operating image area, and a movement amount from an actual current position of a front end of the probe to a target position thereof is calculated by designating each of the actual current position of the front and of the probe and the target position of the front and of the probe on the probe information image so that the probe controller operates in accordance with the movement amount to move the probe to the target position.

JP-A-2000-181898 discloses a probe apparatus including a charged particle beam projection device, a specimen stage for holding a specimen holder with a specimen thereon, a specimen chamber containing the specimen stage, a probe driving mechanism for moving the probe to contact the specimen in the specimen chamber, a specimen antechamber including a first stocker connected through a valve to the specimen chamber to store temporarily the specimen holder, and a first transfer device for moving the specimen holder at least between the specimen antechamber and the specimen chamber.

JP-A-2002-523784 discloses that an optical microscope slides on a microscope bridge to move to a position on a wafer chuck, and is rotated to a position for preventing from standing in the way of enabling the probe to firstly be positioned in an area of the specimen to which an user's attention is drawn.

BRIEF SUMMARY OF THE INVENTION

An object of the present invention is to provide a defective product inspection apparatus and method for adjusting a positional relationship between a specimen and a probe, by which apparatus and method an electric characteristic of the specimen can be measured efficiently (with making a time period needed for the inspection as small as possible) while the specimen is restrained from being damaged.

According to the invention, a defective product inspection apparatus for measuring an electric characteristic of a specimen through (or with) a contact between a probe and the specimen (so that the measured electric characteristic is compared with a predetermined electric characteristic to judge whether the specimen as a product is defective or not), comprises, a specimen table for holding the specimen thereon, a probe holder for holding the probe thereon, a first measuring device for measuring a positional relationship between the probe and the specimen, and a second measuring device for measuring the positional relationship between the probe and the specimen, wherein (a measuring accuracy (resolution capability, magnification or the like) of the second measuring device is superior to a measuring accuracy (resolution capability, magnification or the like) of the first measuring device,) the apparatus further includes a base table holding thereon the specimen table and the probe holder in such a manner that the specimen table and the probe holder are movable with respect to each other on the base table to adjust the positional relationship between the probe and the specimen on the base table so that a contact area of the probe and a desired area of the specimen are capable of being brought into contact with each other, and the base table is movable between (or from) a first position at which the positional relationship between the probe and the specimen is measurable by the first measuring device and (or to) a second position at which the positional relationship between the probe and the specimen is measurable by the second measuring device. Incidentally, the specimen table is movable with respect to the base table, and the probe holder is movable with respect to the base table, so that a positional relationship between the specimen table and the base table and a positional relationship between the probe holder and the base table are adjustable independent of each other, and one of the positional relationship between the specimen table and the base table and the positional relationship between the probe holder and the base table is adjustable when the other one the positional relationship between the specimen table and the base table and the positional relationship between the probe holder and the base table is stationary.

Since (the measuring accuracy of the second measuring device is superior to the measuring accuracy of the first measuring device, and) the a base table holding thereon the specimen table and the probe holder in such a manner that the specimen table and the probe holder are movable with respect to each other on the base table to adjust the positional relationship between the probe and the specimen on the base table so that a contact area of the probe and the desired area of the specimen are capable of being brought into contact with each other, and the base table is movable between (or from) the first position at which the positional relationship between the probe and the specimen is measurable by the first measuring device and (or to) the second position at which the positional relationship between the probe and the specimen is measurable by the second measuring device, a time period which is needed for measuring the positional relationship between the probe and the specimen at the second position with the measuring accuracy superior to the measuring accuracy at the first position can be decreased by the measurement at the first position, so that the electric characteristic of the specimen can be measured efficiently. If the probe and the specimen are brought into contact with each other at the second position, a time period which is needed for bringing the probe and the specimen into contact with each other at the second position can be minimized, so that the electric characteristic of the specimen can be measured efficiently. The base table may be movable with respect to at least one (or each) of the first and second measuring devices.

If the first measuring device is capable of measuring the positional relationship between the probe and the specimen when the specimen is prevented from being irradiated with at least one of an ion beam and an electron beam, the specimen is prevented from being damaged by the at least one of the ion beam and the electron beam. If the second measuring device is capable of measuring the positional relationship between the probe and the specimen by irradiating the specimen with at least one of an ion beam and an electron beam, the specimen is restrained from being damaged by the at least one of the ion beam and the electron beam, by the decrease of the time period for at least one of measuring the positional relationship between the probe and the specimen at the second position and bringing the probe and the specimen into contact with each other at the second position.

The first measuring device may be capable of measuring the positional relationship between the probe and the specimen in each of first and second directions perpendicular to each other, so that the distance between the probe and the specimen in each of first and second directions perpendicular to each other can be measured to increase the accuracy for measuring the positional relationship. If the first direction is parallel to a thickness direction of the specimen, the first measuring device has a first magnification for magnifying an image corresponding to the positional relationship between the probe and the specimen in the first direction and a second magnification for magnifying another image corresponding to the positional relationship between the probe and the specimen in the second direction, and the first magnification is higher than the second magnification so that a contact or distance between the probe and specimen in the first direction is measurable more accurately in comparison with an overlap or distance between the probe and specimen in the second direction, the time period for at least one of measuring the positional relationship between the probe and the specimen at the second position and bringing the probe and the specimen into contact with each other at the second position can be decreased so that the electric characteristic of the specimen can be measured efficiently.

The defective product inspection apparatus may further comprises a specimen chamber being capable of being kept in vacuumed condition and containing therein the first and second positions (more preferably also a third position as described below) in such a manner that the probe and the specimen are kept (continuously) in the vacuum environment of the specimen chamber (to prevent the probe and the specimen from taken out from the vacuum environment, that is, the specimen chamber of vacuumed condition containing therein the first, second and third positions), while the base table is moved between (or from) the first position and (or to) the second position, so that the specimen is prevented completely by the vacuumed condition of the specimen chamber from being damaged by an environment matter surrounding the specimen chamber.

The apparatus further may comprise a third position at which the probe is replaced by another probe, and the base table may be movable among the first, second and third positions in the specimen chamber, so that the specimen is prevented completely by the vacuumed condition of the specimen chamber from being damaged by the replacement or exchange of the probe. It is preferable for increasing the efficiency for measuring the electric characteristic of the specimen that a distance between the first and second positions is shorter than a distance between the second and third positions.

The first measuring device may include at least one of an optical microscope and a CCD camera.

If the probe and the specimen are capable of (manually or automatically): being moved with respect to each other at least in a first direction parallel to the thickness direction of the specimen, while the positional relationship between the probe and the specimen is measured at the first position by the first measuring device, to be positioned to respective adjacent (relative) positions at which (a distance between the contact area of the probe and the desired area of the specimen is not more than a predetermined value (may be zero for making the contact area of the probe and the desired area of the specimen overlap at least partially each other) as seen in a first direction parallel to a thickness direction of the specimen and the contact area of the probe, and/or a distance between or among the probes is as seen in the first direction is not more than a predetermined value and being more than zero and) the desired area of the specimen are separated from each other to form therebetween a clearance of value being not more than a predetermined value (as small as possible) and being more than zero in the first direction, and subsequently being moved with respect to each other at least in the first direction to bring the contact area of the probe and the desired area of the specimen into contact with each other while the positional relationship between the probe and the specimen is measured at the second position by the second measuring device, the time period for at least one of measuring the positional relationship between the probe and the specimen at the second position and bringing the probe and the specimen into contact with each other at the second position can be minimized so that the electric characteristic of the specimen can be measured efficiently, and the specimen is restrained from being damaged at the second position (by at least one of ion beam or electron beam).

It is preferable for decreasing the time period for at least one of measuring the positional relationship between the probe and the specimen at the second position and bringing the probe and the specimen into contact with each other at the second position that the positional relationship between the probe and the specimen is fixed while the base table moves from the first position to the second position.

It is preferable for correctly bringing the contact area of the probe and the desired area of the specimen into contact with each other that the positional relationship between the probe and the specimen is a positional relationship between the contact area of the probe and the desired area of the specimen.

According to the invention, in a method for adjusting a positional relationship between a specimen and a probe to measure an electric characteristic of the specimen through (or with) a contact between the probe and the specimen (so that the measured electric characteristic is compared with a predetermined electric characteristic to judge whether the specimen as a product is defective or not), comprises the steps of: positioning a base table holding thereon a specimen table holding the specimen and a probe holder holding the probe, at a first position to measure the positional relationship between the probe and the specimen at the first position, and subsequently positioning the base table at a second position to measure the positional relationship between the probe and the specimen at the second position so that a contact area (preferably a front end) of the probe and a desired area of the specimen are capable of contacting each other at the second position, the base table holds the specimen table and the probe holder at each of the first and second positions in such a manner that the specimen table and the probe holder are movable with respect to each other on the base table to adjust the positional relationship between the probe and the specimen, and a measuring accuracy (resolution capability, magnification or the like) at the second position is superior to a measuring accuracy (resolution capability, magnification or the like) at the first position. Incidentally, the specimen table is movable with respect to the base table, and the probe holder is movable with respect to the base table, so that a positional relationship between the specimen table and the base table and a positional relationship between the probe holder and the base table are adjustable independent of each other, and one of the positional relationship between the specimen table and the base table and the positional relationship between the probe holder and the base table is adjustable when the other one the positional relationship between the specimen table and the base table and the positional relationship between the probe holder and the base table is stationary.

Since the base table holds the specimen table and the probe holder at each of the first and second positions in such a manner that the specimen table and the probe holder are movable with respect to each other on the base table to adjust the positional relationship between the probe and the specimen, and the measuring accuracy (resolution capability) at the second position is superior to a measuring accuracy (resolution capability) at the first position, a time period which is needed for measuring the positional relationship between the probe and the specimen at the second position with the measuring accuracy (resolution capability) superior to the measuring accuracy (resolution capability) at the first position can be decreased by the measurement at the first position, so that the electric characteristic of the specimen can be measured efficiently.

It is preferable for minimizing the time period for at least one of measuring the positional relationship between the probe and the specimen at the second position and bringing the probe and the specimen into contact with each other at the second position, that the probe and the specimen are capable of being moved with respect to each other at least in a first direction parallel to the thickness direction of the specimen at the first position, while the positional relationship between the probe and the specimen is measured, to be positioned to respective adjacent (relative) positions at which (a distance between the contact area of the probe and the desired area of the specimen is not more than a predetermined value (may be zero for making the contact area of the probe and the desired area of the specimen overlap at least partially each other) as seen in a first direction parallel to a thickness direction of the specimen and/or a distance between or among the probes as seen in the first direction is not more than a predetermined value and being more than zero, and) the contact area of the probe and the desired area of the specimen are separated from each other to form therebetween a clearance of value being not more than a predetermined value (as small as possible) and being more than zero in the first direction, and subsequently the probe and the specimen are moved with respect to each other at least in the first direction at the second position to bring the contact area of the probe and the desired area of the specimen into contact with each other while the positional relationship between the probe and the specimen is measured.

If at the first position, the positional relationship between the probe and the specimen is measured when the specimen is prevented from being irradiated with at least one of an ion beam and an electron beam, the specimen is prevented from being damaged by the at least one of the ion beam and the electron beam. If at the second position, the positional relationship between the probe and the specimen is measured while irradiating the specimen with at least one of an ion beam and an electron beam, the specimen is restrained from being damaged by the at least one of the ion beam and the electron beam, by the decrease of the time period for at least one of measuring the positional relationship between the probe and the specimen at the second position and bringing the probe and the specimen into contact with each other at the second position.

If at the first position, the positional relationship between the probe and the specimen in each of first and second directions perpendicular to each other is measured, the first direction is parallel to a thickness direction of the specimen, and a first magnification for magnifying an image corresponding to the positional relationship between the probe and the specimen in the first direction is higher than a second magnification for magnifying another image corresponding to the positional relationship between the probe and the specimen in the second direction (so that a contact or distance between the probe and specimen in the first direction is measurable more accurately in comparison with an overlap or distance between the probe and specimen in the second direction), a contact or distance between the probe and specimen in the first direction is measurable more accurately in comparison with an overlap or distance between the probe and specimen in the second direction, and the time period for at least one of measuring the positional relationship between the probe and the specimen at the second position and bringing the probe and the specimen into contact with each other at the second position can be decreased so that the electric characteristic of the specimen can be measured efficiently.

If a vacuum environment is kept around the base table so that the probe and the specimen are kept (continuously) in the vacuum environment (to prevent the probe and the specimen from taken out from the vacuum environment, that is, the specimen chamber of vacuumed condition containing therein the first, second and third positions) while the base table is moved between (or from) the first position and (or to) the second position, the specimen is prevented completely by the vacuumed condition of the specimen chamber from being damaged by an environment matter surrounding the specimen chamber.

If the base table is moved among the first position, the second position and a third position at which the probe is replaced by another probe in the specimen chamber, the specimen is prevented completely by the vacuumed condition of the specimen chamber from being damaged by the replacement or exchange of the probe.

If the positional relationship between the probe and the specimen is fixed while the base table moves from the first position to the second position, the time period for at least one of measuring the positional relationship between the probe and the specimen at the second position and bringing the probe and the specimen into contact with each other at the second position can be decreased.

Other objects, features and advantages of the invention will become apparent from the following description of the embodiments of the invention taken in conjunction with the accompanying drawings.

BRIEF DESCRIPTION OF THE SEVERAL VIEWS OF THE DRAWINGS

FIG. 3 is a side view of the defective product inspection apparatus in which a slide base is drawn out from a specimen chamber.

FIG. 10A is a schematic partially cross sectional view showing the movable stage under an electron microscope for finish or fine positioning between the specimen and the probe with projecting the electron beam to the specimen, FIG. 10B is a schematic partially cross sectional view showing the movable stage under an optical microscope enabling a rough approach or positioning between the specimen and the probe without projecting the electron beam to the specimen, and FIG. 10C is a schematic partially cross sectional view showing the movable stage under a probe exchange mechanism.

DETAILED DESCRIPTION OF THE INVENTION

Figure 1:
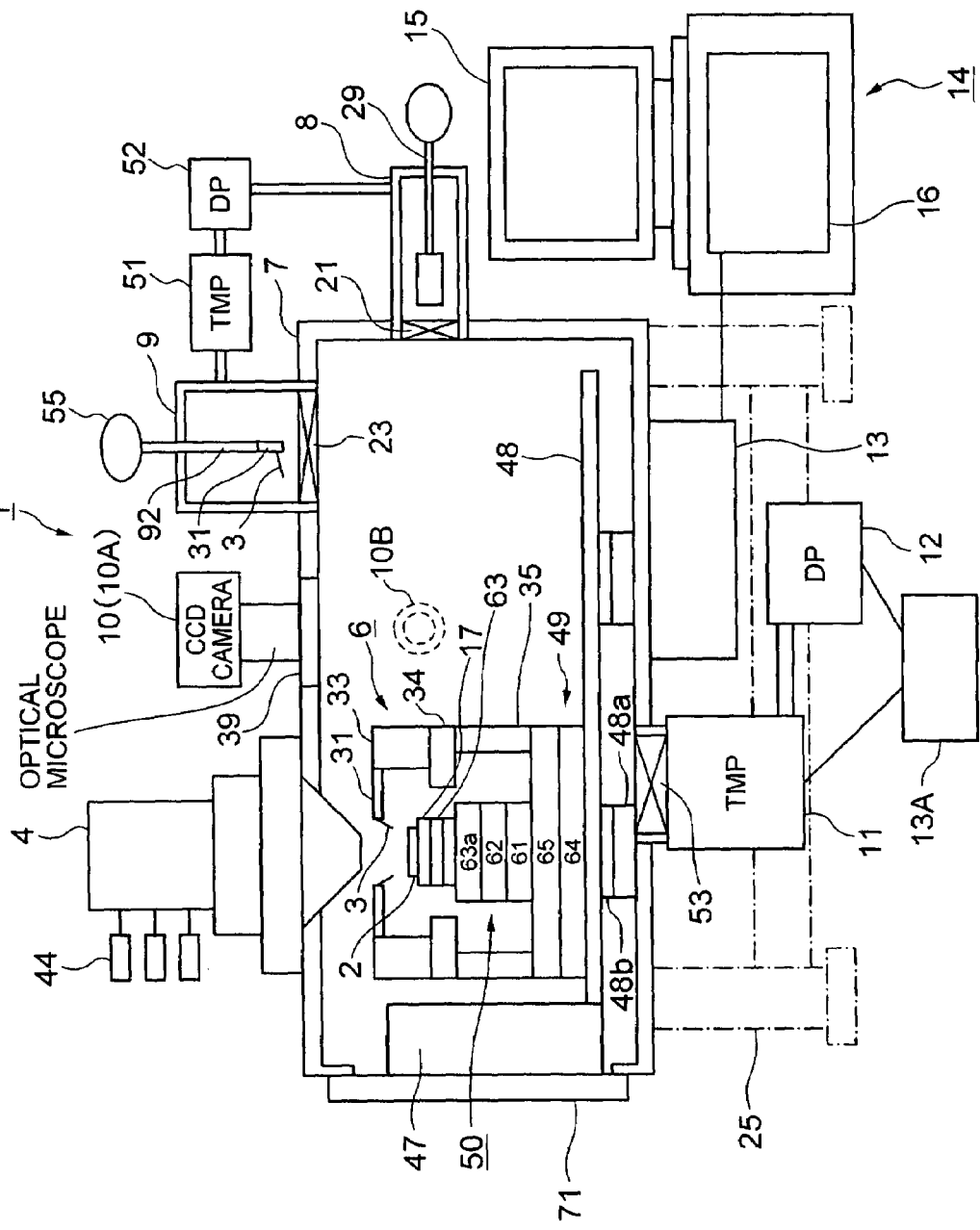
FIG. 1 is a cross sectional view showing a defective product inspection apparatus.

As shown in FIG. 1, a defective product inspection device 1 has a specimen chamber 7 containing a specimen stage including a specimen holder 2 on which a specimen is to be held, and a specimen holder receiver 17 holding the specimen holder 2, and a probe stage 6 including a probe unit 33. An electronic optical device 4 (a charged particle apparatus) such as an SEM (scanning electron microscope), a focused ion beam (FIB) device or the like including an ion pump 44 is arranged on a frame of the specimen chamber 7 to opposite to the specimen holder 2. Further, a probe rough-approaching image forming device 10 is arranged in the vicinity of the electronic optical device 4. A charged particle beam (electron beam or ion beam) is projected from the electronic optical device 4 toward the specimen holder to monitor movements of the specimen and a probe 3.

The probe rough-approaching image forming device 10 arranged in the vicinity of the electronic optical device 4 on an upper surface of the frame of the specimen chamber 7 has a probe rough-approaching optical microscope and a CCD camera for obtaining an image so that a condition in rough approach of the probe 3 with respect to the specimen is monitored by obtaining its image. Further, the probe rough-approaching image forming device 10 has a probe rough-approaching image forming device 10a for monitoring in a vertical direction and a probe rough-approaching image forming device 10b for monitoring in a horizontal direction, so that the condition in rough approaching between the prove and the specimen can be monitored securely in two directions perpendicular to each other. In this case, a magnification of the probe rough-approaching image forming device 10b for magnifying the image corresponding to the condition in rough approaching as seen in the horizontal direction is made higher than a magnification of the probe rough-approaching image forming device 10a for magnifying the image corresponding to the condition in rough approaching as seen in the vertical direction, because the image corresponding to the condition in rough approaching obtained by the probe rough-approaching image forming device 10a needs to include a plurality of the probes 3 which need to be approached each other and horizontally positioned over respective areas of the specimen so that at least one electric characteristic of the specimen is detected from the areas of the specimen after the probes 3 are brought into contact with the areas of the specimen respectively. Each of the probes is moved downwardly to a position adjacent to the specimen while monitoring the image corresponding to the condition in rough approaching as seen in the horizontal direction, and the probes are moved to be adjacent to each other and be separated from each other with a slight distance therebetween or thereamong as seen in the vertical direction. Subsequently, each of the probes is brought into contact with the respective one of the areas of the specimen by moving downwardly each of the probes while monitoring a difference between a focusing condition of each of the probes and a focusing condition of the corresponding one of the areas of the specimen to be decreased in an image as seen in the vertical direction formed by the electronic optical device 4, that is, while monitoring a focusing position of the electronic optical device 4 at which each of the probes is focused and a focusing position of the electronic optical device 4 at which the corresponding one of the areas of the specimen or an area closely adjacent to the corresponding one of the areas of the specimen is focused. If a distance between each of the probes and the corresponding one of the areas of the specimen is made as small as possible before the downward movement of each of the probes on the basis of the image formed by the electronic optical device 4, a time period for the downward movement of each of the probes for the contact between each of the probe and the corresponding one of the areas of the specimen on the basis of the image formed by the electronic optical device 4 can be small to decrease an amount of the charged particle beam with which the specimen is irradiated by the electronic optical device 4. Therefore, the magnification of the probe rough-approaching image forming device 10b is made higher than the magnification of the probe rough-approaching image forming device 10a to improve an accuracy for measuring a positional relationship between each of the probes and the corresponding one of the areas of the specimen.

Figure 2A:
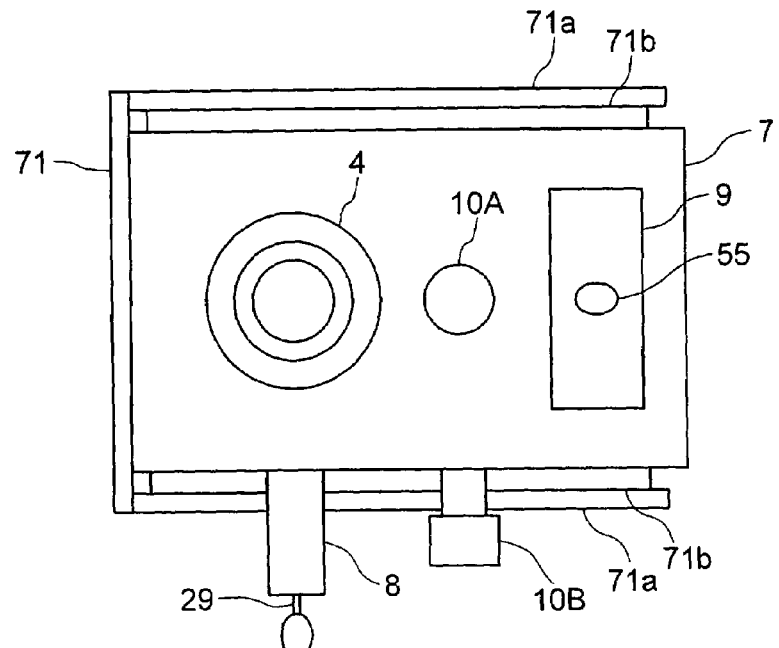
FIG. 2A is a horizontal projection view of the defective product inspection apparatus and FIG. 2B is a side view thereof.
Figure 2B:
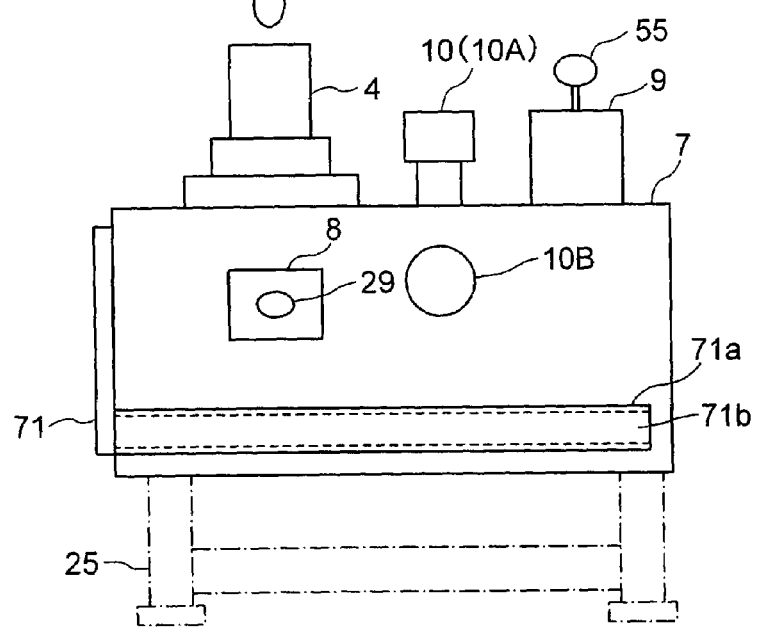

A stage includes a base table 49 on which a specimen stage 50 on which the specimen holder 2 for holding the specimen is mounted and the probe unit 33 are mounted, and a base plate 48 on which the base table 49 is guided linearly and moved horizontally to position a combination of a set of the probes and the specimen at desired one of a fine or finish positioning position just under the electronic optical device 4 for measuring extremely accurately the positional relationship between each of the probes (preferably the front end contacting areas of the probes) and the corresponding one of the areas of the specimen and bringing each of the probes into contact with corresponding desired electrode of the specimen by moving each of the probes (preferably with an extremely slight adjustment of the positional relationship between each of the probes and the corresponding desired electrode of the specimen as seen in the thickness direction of the specimen), a rough-approaching positioning position just under the probe rough-approaching image forming device 10 for measuring the positional relationship between or among the probes and the positional relationship between each of the probes and the specimen and positioning each of the probes or the set of the probes with respect to the specimen to make a distance between or among the probes to be included by an area as seen in the direction parallel to the thickness direction not more than a visible or measurable scope of the electronic optical device 4 and to make a distance between each of the probes and the specimen or a distance between the set of the probes and the specimen as seen in another direction perpendicular to the thickness direction not more than a predetermined value and more than zero so that each of the proves and the set of the probes are separated slightly (as shortly as possible while keeping a minimum distance or clearance therebetween) from the specimen as seen in another direction perpendicular to the thickness direction of the specimen, and a probe exchange position just under a probe exchange chamber 9 for removing desired one of the prove holders 31 including the respective probes 3 from corresponding one of the probe units 33 to be withdrawn into the probe exchange chamber 9 and subsequently bringing a substitute one of the probe holders 31 from the probe exchange chamber 9 to be set onto the corresponding one of the probe units 33. The stage is attached to a side surface of the specimen chamber 7 through a plate 71. As shown in FIG. 2, the plate 71 is movably supported on the specimen chamber 7 by a guide connecting plate 71a and a roller guide 71b. As shown in FIG. 3, the stage is drawn out of the specimen chamber 7 along the roller guide 71b when a maintenance of the stage is done or the probe unit is exchanged. Guide blocks 48a attached to a lower surface of the specimen chamber 7 support vertically the stage through sliding members 48b of low-friction high polymer material between upper surfaces of the guide blocks 48a and a lower surface of the base plate 48.

The probe stage 6 has the probe units 33 including the probe holders 31 for holding the probes 3 respectively, a probe unit base 34 on which the probe units 33 are mounted and a probe unit bracket 35 connecting the probe unit base 34 to the base table 49. Each of the probe units 33 can generates a movement of respective one of the probes 3 in three directions perpendicular to each other with respect to the probe unit base 34 fixed to the base table 49. The base plate 48 can be fixed to the side wall of the specimen chamber 7 by a fixing member 47. The specimen chamber 7 includes a specimen exchange chamber 8 and the probe exchange chamber 9.

The plate 71 includes a feed-through to supply a signal for controlling the probe driving motion of each of the probe units 33, and a signal for controlling a motion of each of x, y, z tables 61, 62, 63 of the specimen stage 50 into the specimen chamber 7.

Although the specimen exchange chamber 8 is arranged on a right side surface in FIG. 1, the specimen exchange chamber 8 may be arranged at a front side surface in the vicinity of the electronic optical device 4 so that the specimen can be exchanged easily when the specimen table is under the electronic optical device 4. An inside of the specimen exchange chamber 8 and an inside of the specimen chamber 7 are connected to each other by a gate valve 21. The inside of the specimen exchange chamber 8 is connected by a dry pump 52 to be vacuumed. Therefore, the exchange of the specimen holder with the specimen thereon can be performed by a transfer member 29 while a vacuum condition is kept in the specimen chamber 7.

The probe exchange chamber 9 is arranged adjacently to the electronic optical device 4 and the probe rough-approaching image forming device 10a while its distance from the probe rough-approaching image forming device 10a is smaller than its distance from the electronic optical device 4. An inner side of the probe exchange chamber 9 is connected to the inside of the specimen chamber 7 through a gate valve 23. The probe exchange chamber 9 is fluidly connected to a turbo molecular pump (TMP) 51 and the dry pump (DP) 52 connected to the turbo molecular pump to perform a vacuuming operation. While maintaining a high vacuum in the specimen chamber 7, the probe holder 31 is exchanged by an exchange mechanism 55. The specimen chamber 7 is fluidly connected to the TMP 11 through a gate valve 53 and the TMP 11 is connected to DP 12. A frame of the specimen chamber 7 is supported by a bracket 25 shown by an alternate long and short dash line. A control device 13 including a probe unit control part and a stage control part and another control device 13A for controlling a high vacuuming operation of the TMP 11 and DP 12 are arranged. The control device 13A controls also TMP 51 and DP 52.

Further, the defective product inspection apparatus 1 includes a display device 14 including an image display part 15 and an image display control part 16, and a probe operation signal and a stage operation signal from the image display control part 16 are transmitted to the probe unit control part and the stage control part to control the probe units 33 and the stage.

The probe is exchanged, after the x and Y tables of the probe unit to be exchanged are positioned at respective predetermined positions (for example, back end positions), and the z table thereof is positioned at a predetermined position (for example, upper most end position).

The specimen stage 50 is driven to position an area of the specimen which should be made visible on the image display part 15 for displaying the image generated by the electronic optical device 4, that is, needs to be contacted by the probes, into the visible or measurable scope of the electronic optical device 4 for monitoring both the set of the probes and the area of the specimen after the base table 49 is moved on the base plate 48 and the X-Y tables 64 and 65 are driven so that the set of the proves is positioned in the visible or measurable scope of the electronic optical device 4, and subsequently each of the probes 3 is brought into contact with the corresponding one of the electrodes on the area of the specimen by driving the x, y and z tables of the corresponding one of the probe units 33 while monitoring each of the probes and the specimen on the image display part 15. The condition in contact and distance between the probe and the electrode of the specimen in the direction parallel to the thickness direction of the specimen is measurable from the focusing conditions of the electronic optical device 4 on the front end (contact area) of the probe and the electrode surface or a surface area of the specimen closely adjacent to the electrode surface, that is, a focusing position of the electronic optical device 4 at which the front end (contact area) of the probe is focused and a focusing position of the electronic optical device 4 at which the electrode surface or the surface area of the specimen closely adjacent to the electrode surface is focused.

A drive mechanism for the probes and the stages are not necessarily limited, but the drive mechanism for the probes may have a piezo-electric element, DC motor or ultrasonic motor, and the drive mechanism for the stages may have a pulse motor, DC motor or ultrasonic motor.

1. Structure and Operation of Each Element

(1) Probe 3 and Probe Unit 33

Figure 4:
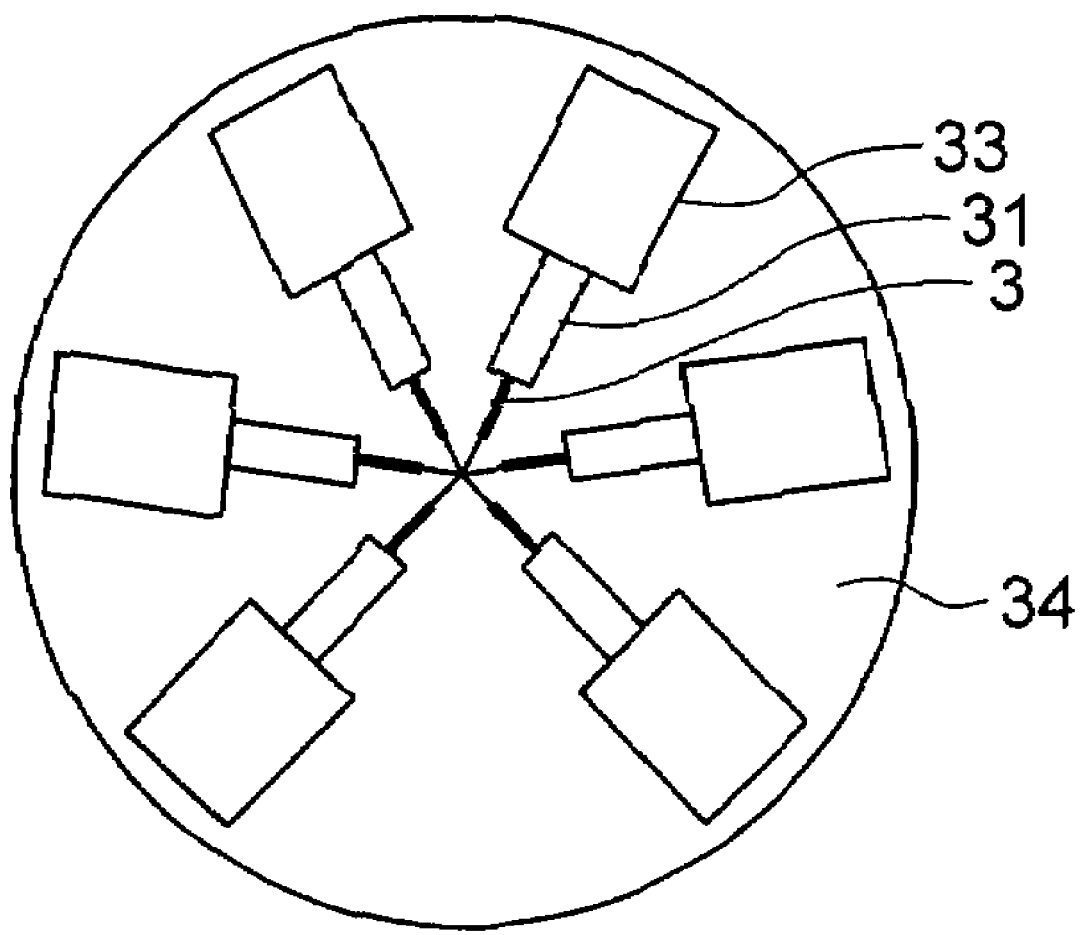
FIG. 4 is a horizontal projection view showing an arrangement of probes.

As shown in FIG. 4, the probes 3 (six in FIG. 4) are held by the probe holders 31 respectively to form six of the probe units 31 respectively to be supported on the probe unit base 34.

Figure 5A:
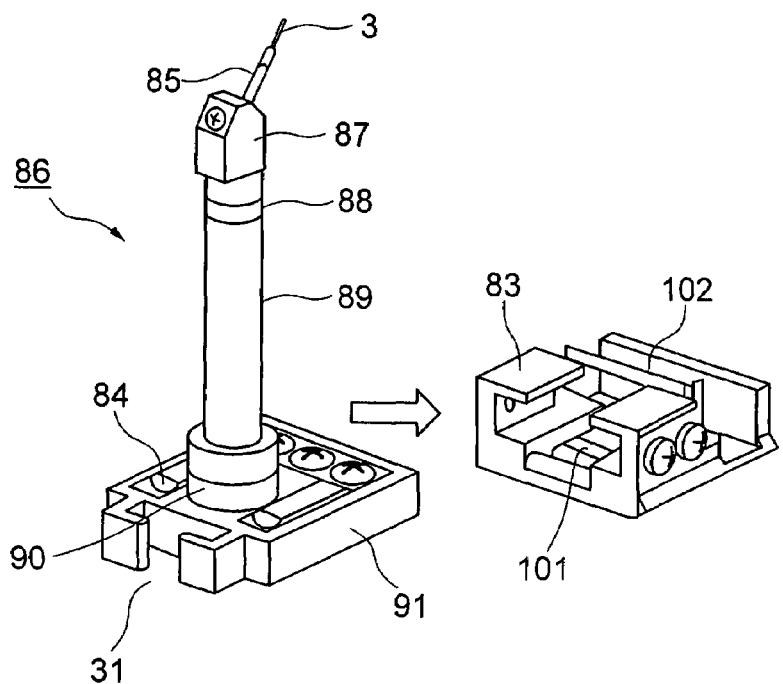
FIG. 5A is a schematic oblique projection view showing a probe holder and a probe unit.
Figure 5B:
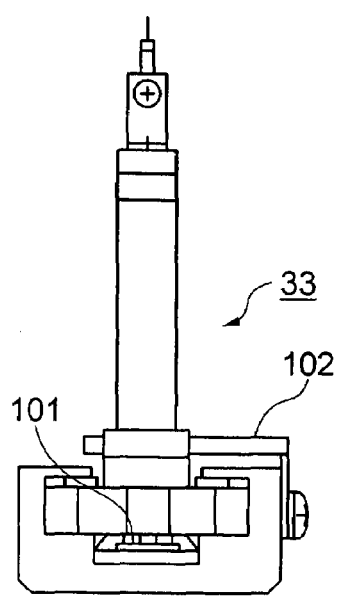
FIG. 5B is a side view of an assembly of the probe holder and the probe unit.

FIG. 5 shows in detail the probe holder and the probe unit. As shown in (a) part of FIG. 5, the probe holder 31 is inserted into the z table 83 of the probe unit 33 and held stationarily thereto by a plate spring 84. An assembled condition of the probe unit 33 is shown in (b) part of FIG. 5. The probe holder 31 includes the probe 3 to be contacted with the specimen, a probe support bar 85 for fixing the probe 3 and a probe arm 86 for fixing the probe support bar 85. The probe support bar 85 has a tubular shape. The probe arm 86 includes a support bar fixing member 87, an insulating ring 88, a connection pipe 89 and an insulating ring 90, and the insulating ring 90 is connected to a probe holder base 91. The support bar fixing member 87 is isolated from the connection pipe 89 by the insulating ring 88, and the connection pipe 89 is isolated from the probe holder base 91 by the insulating ring 90. The support bar fixing member 87 extends in the connection pipe 89 to a back surface of the probe holder base 91 to contact a probe signal outlet electrode 101 when the probe holder 31 is inserted in the z table 83. The probe signal outlet electrode 101 is isolated from the z table 83. The connection pipe 89 contacts a guard signal outlet electrode 102 when the probe holder 31 is inserted in the z table 83. A grounded signal is obtained from the z table 83. The probe signal from the probe signal outlet electrode 101, the guard signal from the guard signal outlet electrode 102 and the grounded signal from the z table 83 are connected to a three-phase coaxial cable, taken out from the specimen chamber 7 through a three-phase coaxial hermetic connector mounted on the specimen chamber 7, and connected through the three phase coaxial cable to an electric characteristic measuring apparatus such as a semiconductor parameter analyzer or the like to measure the electric characteristic.

(2) Stage

The structure of the stage is shown in FIGS. 6-9. The stage includes the base table 49 (as the claimed base table) and the specimen stage 50.

(a) Specimen Stage 50

The specimen stage 50 includes the y table 62, x table 61 and z table 63, 63a to be driven respective driving mechanisms to be moved in respective y, x and z directions to align the area of the specimen within the visible or measurable scope of the electronic optical device 4. Incidentally, the positional relationship among the probes is adjusted by the x and y tables of the prove units 33 in accordance with the positional relationship among the electrodes on the area of the specimen to align the probes respectively with the electrodes on the area of the specimen in the thickness direction of the specimen under the electronic optical device 4 after the positional relationship between or among the probes is adjusted under the probe rough-approaching image forming device 10 so that the probes are included by an area as seen in the thickness direction of the specimen not more than the visible or measurable scope of the electronic optical device 4, and each of the probes is driven in the thickness direction of the specimen by corresponding one of the z tables of the prove units 33 to be brought into contact with the corresponding one of the electrodes under the electronic optical device 4. Under the electrodes under the electronic optical device 4, each of the probes is moved by the y and x tables of the corresponding one of the prove units 33 to make each of the probes and the corresponding one of the electrodes overlap each other as seen in the thickness direction. The x and y tables of the prove units 33 are used to adjust the positional relationship among the probes in accordance with the positional relationship among the desired electrodes of the specimen as seen in the thickness direction of the specimen, and the z tables of the prove units 33 are used to bring each of the probes into contact with the corresponding one of the desired electrodes of the specimen. The x and y tables of the specimen stage 50 are used to align the area including the desired electrodes of the specimen with the visible or measurable scope of the electronic optical device 4, and the z table of the specimen stage 50 may be used to make a distance between the area including the desired electrodes of the specimen and the set of probes (the set of the contact areas of the probes to be positioned in accordance with the positional relationship among the desired electrodes of the specimen) as small as possible under the probe rough-approaching image forming device before bringing each of the probes into contact with the corresponding one of the desired electrodes of the specimen by the z tables of the prove units 33 under the electronic optical device 4.

Figure 7:
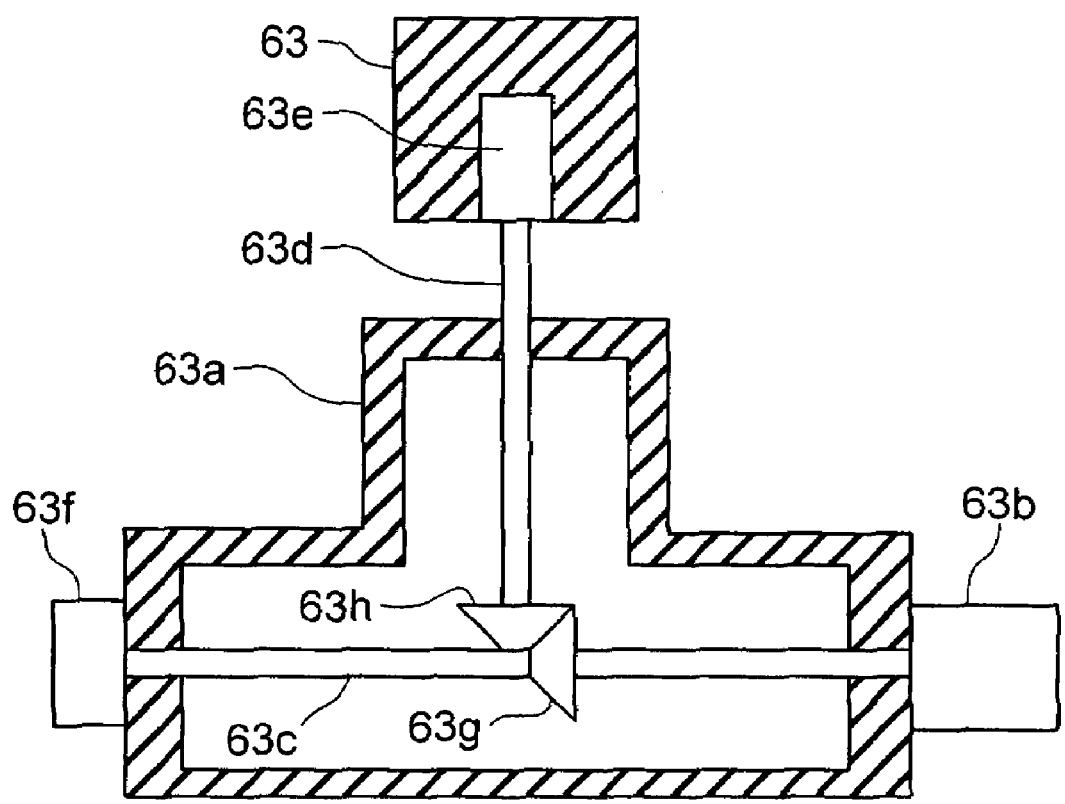
FIG. 7 is a schematic cross sectional view showing a vertically part of the movable stage.
Figure 8A:
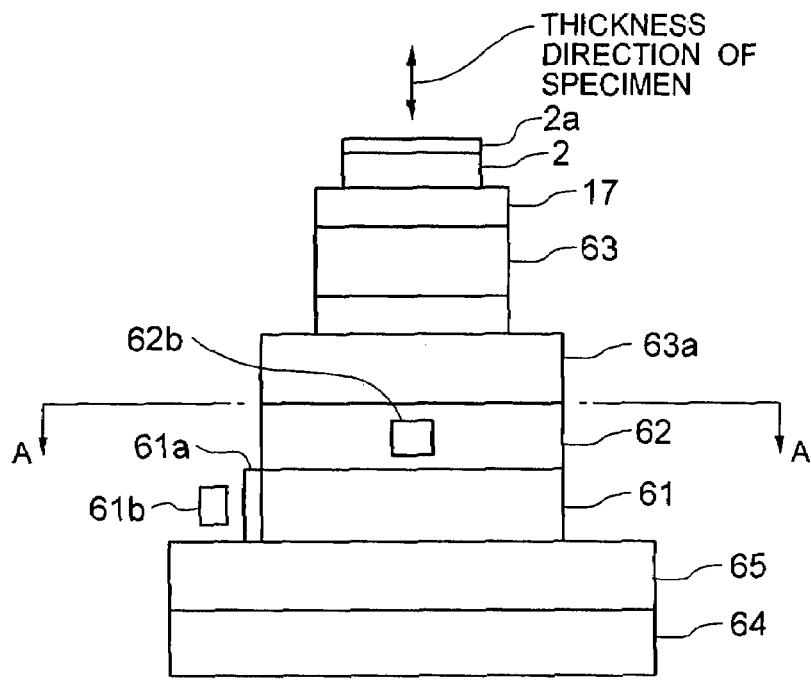
FIG. 8A is a schematic side view of the movable stage.
Figure 8B:
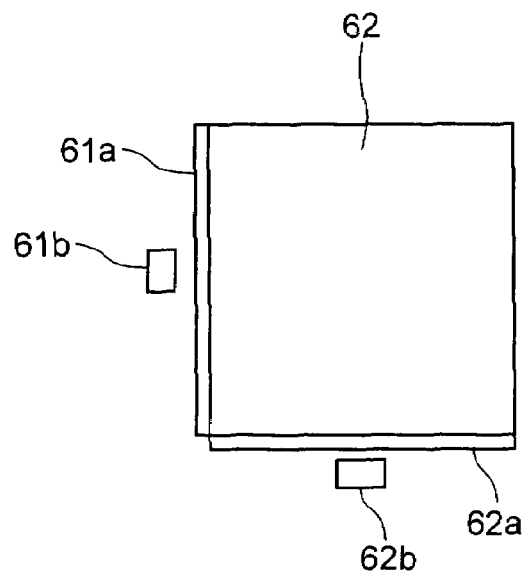
FIG. 8B is a cross sectional view taken along a line A-A' in FIG. 8A.

The y and x tables 62 and 61 are driven by the respective DC motors through respective ball-screws in the specimen chamber and guided by cross-roller guides. As shown in FIG. 7, the z table 63 is moved by driving a ball screw 63e by the DC motor 63b mounted on the z table body 63a through bevel gears 63g, 63h and shafts 63c, 63d. The z table is guided linearly by a cross-roller guide. The specimen holder 2 for holding a specimen 2a is fixed to the specimen holder receiver 17 mounted on the z table 63. Therefore, the specimen 2a is movable with respect to an electron beam 69 in x, y and z directions. The specimen holder 2 on the z table 63 is movable among a measuring position, a specimen exchange position and a probe exchange position. The measuring position is a position at which a distance between the probe and the specimen 2a is decreased to be made as small as possible under the probe rough-approaching image forming device 10 and the probe is brought into contact with the specimen 2a under the electronic optical device 4, the specimen exchange position is a position lower than the measuring position, and the probe exchange position is a position lower than the specimen exchange position, so that an undesirable contact between the probe 3 and the specimen 2a is prevented during each of the probe exchange operation and the specimen exchange operation. The stage 50 may includes a positional sensor such as a linear scale, an encoder or the like to measure quantitatively the position of each of the tables of the stage 50 during the operations, so that an accuracy and repeatability of the movement is obtainable. Examples of arrangement of the positional sensors are shown in FIGS. 7 and 8. The positional condition of the z table is measurable by the encoder 63f connected to the shaft 63c as shown in FIG. 7. The positional conditions of the e table 61 and y table 62 are measurable by the linear scales mounted as shown in FIG. 8. The linear scale has mirrors 61a, 62a mounted on the x table 61 and y table 62 and sensor elements 61b, 62b. In this case, the encoder for measuring the rotary angle of the DC motor is used for the z table, and the linear scales are used for the x table 61 and y table 62, but the encoders, linear scales or combinations thereof may be used for all of the tables.

Figure 9:
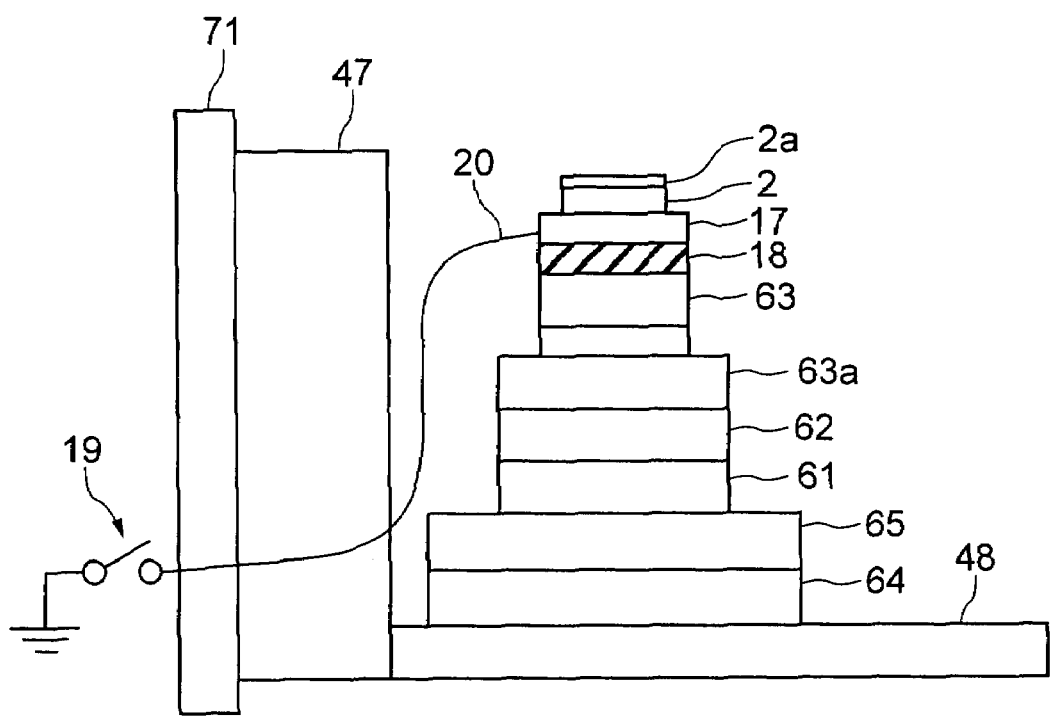
FIG. 9 is a partially cross sectional side view showing the movable stage and a grounded line.
Figure 11A:
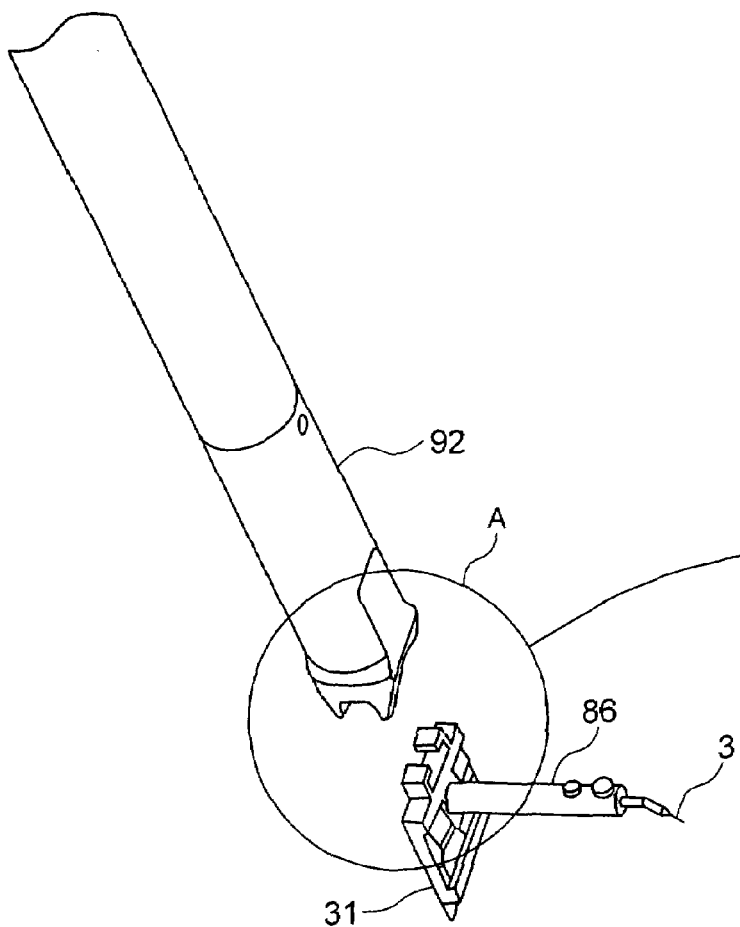
FIG. 11A is an oblique projection view showing a probe exchange rod and a probe holder.
Figure 11B:
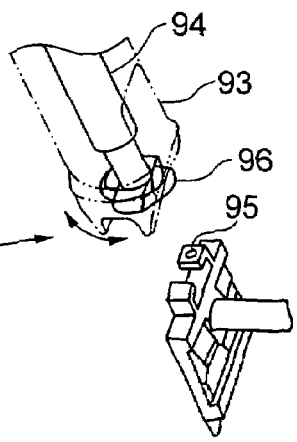
FIG. 11B is an enlarged view of A region of FIG. 11A.

During the monitoring by the SEM, the specimen 2a mounted on the specimen stage 50 is electrically grounded through the specimen stage 50 and the specimen chamber 7 to prevent an effect by a charging up. When an electric characteristic of the specimen 2a is measured, the specimen 2a is preferably isolated electrically from the specimen stage 50 and the specimen chamber 7. Further, for preventing the effect of the charging up, a beam blanking is effective. For the electrical insulation, as shown in FIG. 9, an insulating member 18 is arranged between the specimen holder receiver 17 and the z table 63, the specimen holder receiver 17 with the specimen 2*a* thereon is connected to a cable 20, and the cable 20 extends from the fixing member 47 through the plate 71 to an outside of the vacuumed environment so that the cable 20 is connected to a grounded terminal through a switch 19. By this structure, during the SEM monitoring, the specimen 2*a* is grounded by operating the switch 19 to prevent the effect caused by the noise. Further, by connecting the cable 20 through the switch 19 not to the ground but to an electric characteristic measuring device, the electric characteristic of the specimen 2*a* such as absorption current or the like is measurable without the effect of the noise from the specimen stage 50 and the specimen chamber 7. Further, the specimen holder receiver 17 may includes a guard electrode and a grounded electrode similarly to the probe units 33 and the probe holders 31 as shown in FIG. 5, so that the cable is connected through the three phase coaxial cable to the outside of the vacuumed environment. Therefore, the electric isolation for the specimen 2*a* is improved.

(b) Base Table 49

With making reference to FIG. 10, a process for positioning the specimen 2*a* and the probes 3 in the specimen chamber is explained.

Figure 6:
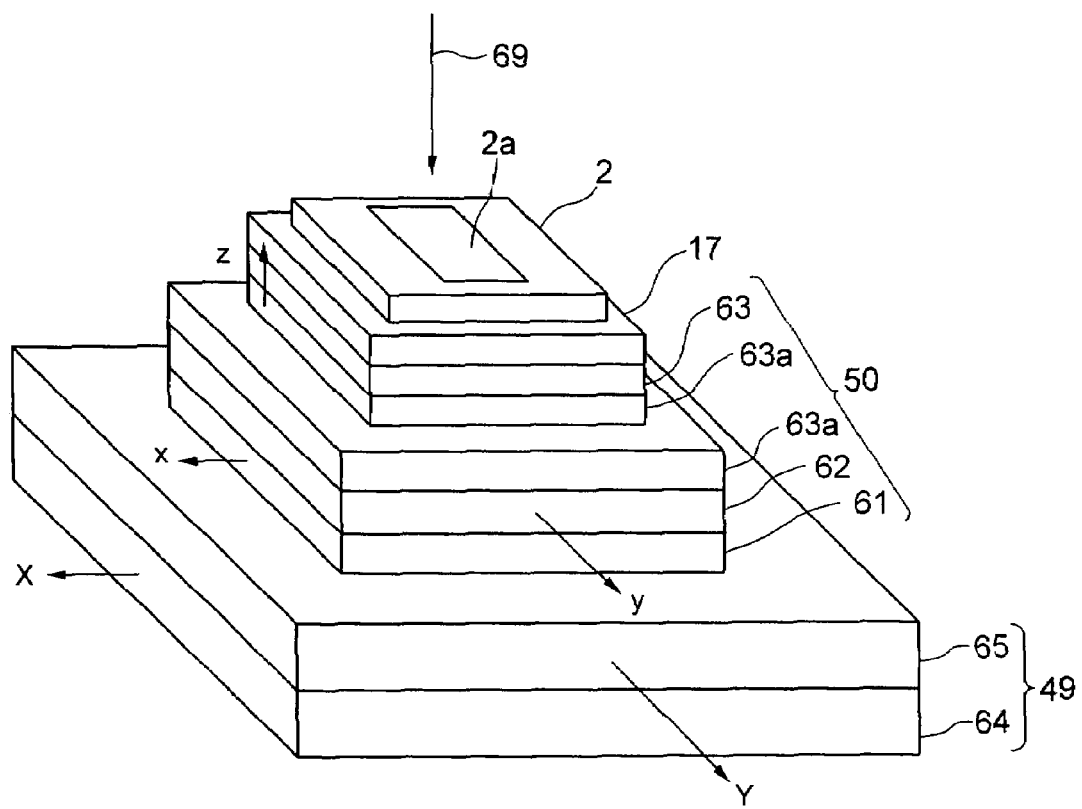
FIG. 6 is a schematic oblique projection view showing a movable stage.

As shown in FIG. 6, the base table 49 includes the Y table 64 and X table 65 to be positioned in y and x directions respectively. The stage 50 and each of the prove holders 31 are mounted on the base table 49 to adjust and fix the positional relationship between the specimen 2*a* and each of the probes on the base table 49.

On the base table 49, the probe units 33 forming the probe stage 6, the probe unit base 34 for supporting the probe units 33 and the probe unit bracket 35 are mounted. Each of the prove units 33 can position the probe in y, x and z directions through the prove holder 31 supported by each of the prove units 33.

As shown in FIG. 10, the base table 49 is moved on the base plate 48 along a linear guide by a ball-screw and a servo motor to position briefly a combination of the specimen and the set of the probes with respect to each of the probe rough-approaching image forming device 10, the electronic optical device 4 and the probe exchange chamber 9. The Y table 64 and X table 65 of the base table 49 position accurately the combination of the specimen and the set of the probes with respect to each of the probe rough-approaching image forming device 10, the electronic optical device 4 and the probe exchange chamber 9.

Therefore, the combination of the specimen and the set of the probes are positioned to each of A position under the electronic optical device 4, B position under the probe rough-approaching image forming device 10 and C position under the probe exchange chamber 9 while the vacuumed environment surrounding the combination of the specimen and the set of the probes is being kept during the movement of the combination of the specimen and the set of the probes among the A, B and C positions within the specimen chamber.

(3) SEM

The SEM arranged on the upper portion of the specimen chamber is an example of the electronic optical device 4 for monitoring the positional relationship between each of the probes (each of the contact areas of the proves) and the corresponding one of the electrodes of the specimen to bring each of the probes in contact with the corresponding one of the electrodes of the specimen. The vacuuming operation for the SEM is performed by the ion pump 44. On the other hand, the probe rough-approaching image forming device 10 including the optical microscope monitors the positional relationship between each of the probes and the corresponding one of the electrodes of the specimen without irradiating the specimen to bring each of the probes to a position close to the corresponding one of the electrodes of the specimen with making a distance (more than zero) between each of the probes and the corresponding one of the electrodes of the specimen as small as possible.

(4) Specimen Chamber 7

The specimen chamber 4 includes an upper cover and a specimen chamber case as the frame, the base 48 is attached to the plate 71 through the fixing member 47 at the side surface of the specimen chamber case, the probe units 33 are mounted on the base table 49 in the specimen chamber, and the specimen exchange chamber 8 is attached to another side surface of the specimen chamber case. The probe rough-approaching image forming device 10, the electronic optical device 4 and the probe exchange chamber 9 are mounted on the upper cover. The specimen chamber 7 is fixed to a bearing plate mounted on a vibration absorbing mount on the bracket 25. The specimen chamber 7 is vacuumed by the turbo molecular pump (TMP) 11 and the dry pump (DP) 12.

(5) Optical Microscope for Rough-approaching, CCD Camera and Rough-approaching Image Forming Device The specimen 2*a* whose electrical characteristic needs to be measured is a semiconductor including plugs generally connected a gate, a source, a drain and a well respectively to be connected by the probes respectively. The plug may have a minimum diameter of tens of nanometers, so that a SEM with high resolution is necessary for bringing the probe into contact with the plug. However, by irradiating the semiconductor specimen with the electron and/or ion beam, there is a probability of that the semiconductor specimen is damaged, so that it is preferable for a time period of irradiating the semiconductor specimen with the electron and/or ion beam to be made as short as possible. Therefore, on the basis of the image of the probe rough-approaching image forming device 10 displayed on the image display part 15, a distance between each of the probes and corresponding one of the plugs (electrodes) of the specimen as seen in the thickness direction of the semiconductor specimen is made as small as possible or preferably zero, and a gap or clearance therebetween as seen in a direction perpendicular to the thickness direction is made as small as possible but is prevented from being zero. This operation is performed while an image showing the positional relationship between the probes and the specimen surface as obtained by the probe rough-approaching optical microscope and the CCD camera attached thereto and displayed on the image display portion 15 is monitored.

The magnification on the image display portion 15 is tens to form an image including the specimen 2*a* and the probes 3 adjacent to each other as close as possible.

A light source is arranged in the vicinity of the probe rough-approaching optical microscope. The monitoring by the probe rough-approaching optical microscope and CCD camera and the light supply from the light source into the specimen chamber is performed through a window aperture 39 as shown in FIG. 1.

(6) Specimen Exchange Chamber 8

The specimen exchange chamber 8 is arranged to exchange the specimen 2*a* while keeping the environment vacuum condition surrounding the specimen 2a in the specimen chamber 7 and vacuumed by the dry pump 52. The specimen exchange chamber 8 can be isolated fluidly from the specimen chamber 7 by the gate valve 21. When the specimen 2a is introduced into the specimen chamber 7, a male screw of a front end of an exchange bar 29 as a transfer member for the specimen 2a and the specimen holder 2 is screwed into a female screw of the specimen holder 2 with the specimen 2a thereon, the gate valve 21 is opened, and the specimen holder 2 is inserted onto the specimen holder receiver 17 attached to an upper end of the z table 63 of the specimen stage 50. When the specimen 2a is taken out of the specimen chamber, a reverse operation is performed. Therefore, a time period for the specimen exchange can be decreased.

(7) Probe Exchange Chamber 9

The probe exchange chamber 9 is arranged to exchange the probe 3 while keeping the environment vacuum condition surrounding the probe 3 in the specimen chamber 7 so that a time period for the probe exchange is decreased. The probe exchange chamber 9 can be isolated fluidly from the specimen chamber 7 by the gate valve 23. The probe exchange chamber 9 is vacuumed by the turbo molecular pump 51 and the dry pump 52. The turbo molecular pump 51 is used to accelerate a vacuuming operation for the probe exchange chamber 9, because if the vacuuming operation for the probe exchange chamber 9 is brought about by the dry pump 52 without the turbo molecular pump 51, a great volume of the probe exchange chamber 9 in which a pressure cannot be decreased sufficiently within a short time period by the dry pump 52 without the turbo molecular pump 51 causes a great increase of the inner pressure of the specimen chamber 7 when the gate valve 23 is opened to exchange the probe 3 so that a time period for making the pressure in the specimen chamber 7 at the same value as the previous pressure before opening the gate valve 23 becomes long.

In the probe exchange chamber 9, a stocker (not shown) for holding the probe holders 31 is arranged and moved by a ball-screw with respect to a probe exchange bar 92. The probe holder 31 is moved below the probe exchange bar 92 to be withdrawn from the stocker or contained in the stocker. A latch key 96 at a lower end of an exchange rod 94 arranged in a probe exchange bar outer tube 93 coaxial with the probe exchange bar 92 is rotated by 90 degrees to engage with a latch receiver 95 on the probe holder 31 to be connected to the probe exchange bar 92. The exchange rod 94 is rotated by 90 degrees in a reverse direction to disengage the latch key 96 from the latch receiver 95. The stocker including the used probe holders 31 is taken out of the probe exchange chamber 9, and unused ones of the probe holders 31 are inserted onto the stocker to be introduced into the probe exchange chamber 9.

When the probe holder 31 is transferred from the stocker to the probe unit 33, the latch key 96 of the probe exchange rod 94 is engaged with the latch receiver 95 on the probe holder 31, and the probe exchange bar 92 is moved upward by a rack-and-pinion mechanism to withdraw the probe holder 31 from the stocker. The gate valve 23 is opened and the probe exchange bar 92 is moved downward to introduce the probe holder 31 into the specimen chamber. As shown in FIG. 5, the holder receiver is arranged on the z table 83 of the probe unit 33. The base table 49 is driven to move the holder receiver below the transferred probe holder 31, the probe exchange bar 92 is rotated to make orientations of the holder receiver and the probe holder 31 consistent with each other, and the exchange bar 92 is moved downward to insert the probe holder 31 into the holder receiver. The latch key 96 is disengaged from the latch receiver 95, the probe exchange bar 92 is moved upward to be withdrawn into the probe exchange chamber 9, and the gate valve 23 is closed.

2. Control System

The SEM, the probe units 33 and the tables of the stages are controlled by respective control circuits and computers contained by the control device 13. The SEM, the probe units 33 and the tables of the stages are controllable from a operating panel or GUI on the monitor.

The control device 13 includes a stage controller for controlling the tables of the stages, and a probe controller for controlling the probe units 33 independent of the stages. The image control part 16 includes a secondary electron detector control part, a control part for the electron beam emitting optical system and so forth. In addition, a calculation treatment part has a function of displaying an image showing the specimen holder, the specimen 2a and the positional relationship between the proves and the specimen 2a.

The probe units 33 and the tables of the stages are driven by operating an operating display of the image display part to supply an operating signal through the image display control part to the probe unit control part and the stage control part. Alternatively, an operating panel including a joy-stick may be used to drive the units 33 and the tables of the stages.

(1) SEM

The electron beam generated by an electron gun is emitted through a condensing lens and an objective lens to the specimen 2a to be irradiated, and the secondary electron generated from the specimen 2a is detected by the secondary electron detector to generate a signal so that the signal is electrically treated variously in the display to form an image of the specimen surface on the monitor on the image display part 15 of the display device 14.

(2) Probe Unit 33

A signal for controlling each of the operations of the x, y and z tables of each of the probe units 33 from the control circuit 13 in the bracket 25 as shown in FIG. 1 is supplied to each of the probe units 33 in the specimen chamber 7 through a feed-through attached the plate 71 of the stages. Input signals supplied to the specimen 2a through the probes 3 attached to the probe holders 31 and output signals generated from the specimen 2a are transmitted with respect to a semiconductor parameter analyzer through a three phase coaxial hermetic connector attached to the specimen chamber 7.

(3) Stages

Signals generated by the control circuit in the bracket 25 to control the operations of the x, y and z tables 61, 62 and 63 of the specimen stage 50 on the base plate 49 are supplied to the specimen stage 50 in the specimen chamber through the feed-through attached to the plate 71. Signals for controlling the operations of the x and y tables 64 and 65 are also supplied to the base plate 49 through the feed-through attached to the plate 71.

3. Display Device 14

The display device 14 displays a rough-approaching image taken by the probe rough-approaching image forming device 10, a contacting image taken by the electron optical device 4 to show a positional relationship between each of the probes and the specimen brought into contact with each other, the probe operating image and an image showing a sequence of the operating.

The user operates the probes 3 and the specimen 2a to be positioned accurately with respect to each other along the sequence of the operating displayed on the display device 14, while monitoring the rough-approaching image and the contacting image.

Figure 12A:
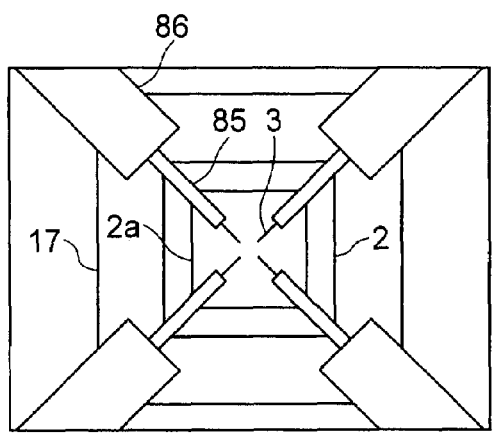
FIG. 12A is a schematic view showing a positional relationship as seen in a vertical direction between the probe and the specimen positioned roughly with respect to each other under the optical microscope.
Figure 12B:
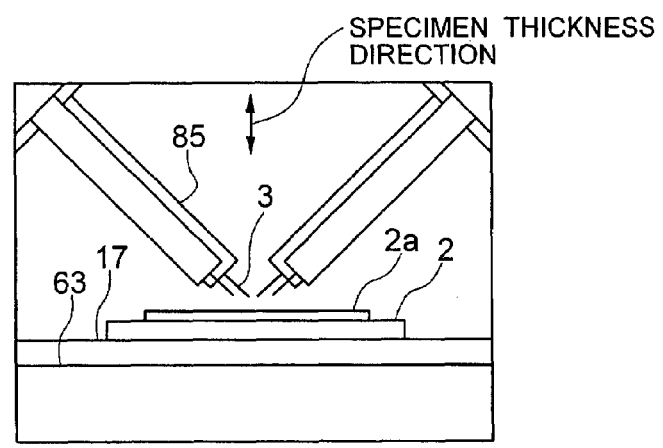
FIG. 12B is a schematic view showing the positional relationship as seen in a horizontal direction between the probe and the specimen positioned roughly with respect to each other under the optical microscope.
Figure 12C:
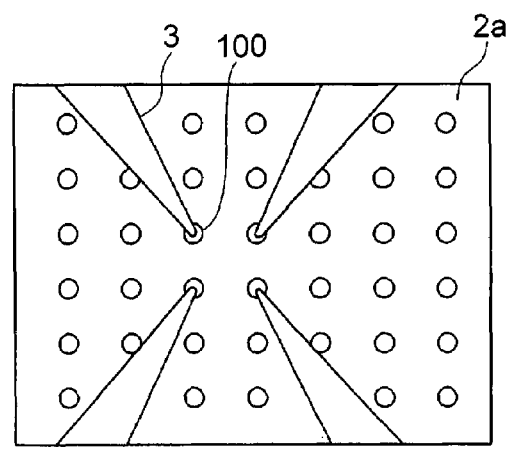
FIG. 12C is an extremely enlarged schematic view showing the positional relationship as seen in the vertical direction between the probe and the specimen positioned finely with respect to each other under the electron microscope.

As shown in FIG. 12A, the rough-approaching image taken by the probe rough-approaching image forming device 10A shows the positional relationship between each the probes and the specimen as seen in the thickness direction of the specimen with the magnification of, for example, 10. As shown in FIG. 12B, the rough-approaching image taken by the probe rough-approaching image forming device 10B shows the positional relationship between each the probes and the specimen as seen in the direction perpendicular to the thickness direction of the specimen with the magnification of, for example, 25 increased by 2.5 times in comparison with the magnification of the rough-approaching image taken by the probe rough-approaching image forming device 10A to enable a distance between each of the probes 3 and the specimen 2a as seen in the direction perpendicular to the thickness direction of the specimen to be made as small as possible but to be prevented from decreasing to zero. As shown in FIG. 12C, the contacting image taken by the electron optical device 4 shows the positional relation ship between each of the probes 3 (each of the contact areas of the probes) and the corresponding one of the electrodes or plugs 100 of the specimen 2a to be brought into contact with each other, with the magnification of thousands to ten-thousands. The electrodes or plugs 100 are connected respectively to the gate, source, drain and so forth in the specimen 2a.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A defective product inspection apparatus for inspecting a product as a specimen, comprising:
   a stage for holding the specimen thereon;
   a specimen chamber for containing the stage therein;
   a probe contactable to the specimen in the specimen chamber;
   a probe holder for holding the probe thereon;
   a probe exchange chamber for containing the probe holder therein;
   a gate valve for connecting the specimen chamber and the probe exchange chamber to each other;
   an exhauster for exhausting air from the specimen chamber and the probe exchange chamber; and
   an electronic optical device for projecting a charged particle beam to the specimen,
   wherein the probe holder is movable on the stage and the stage is movable between a first position in the vicinity of the electronic optical device and a second position in the vicinity of the probe exchange chamber in the specimen chamber.

2. The defective product inspection apparatus according to claim 1, wherein the probe exchange chamber includes an exchange member for transferring the probe holder between the specimen chamber and the probe exchange chamber.

3. The defective product inspection apparatus according to claim 2, wherein:
   the probe exchange chamber is arranged above the specimen chamber; and
   the exchange member is movable vertically to transfer the probe holder.

4. The defective product inspection apparatus according to claim 3, wherein the stage is movable in the specimen chamber between a position for inspecting the specimen and another position for exchange of the probe holder.

5. The defective product inspection apparatus according to claim 2, wherein:
   the exchange member has a latch key and is rotatable; and
   the probe holder has a latch catcher so that the exchange member is rotated to make the latch key engage with the latch catcher.

6. The defective product inspection apparatus according to claim 5, wherein the stage is movable in the specimen chamber between a position for inspecting the specimen and another position for exchange of the probe holder.

7. The defective product inspection apparatus according to claim 2, wherein the probe holder is mounted on the stage.

8. The defective product inspection apparatus according to claim 1, wherein the exhauster includes exhauster parts independent from each other to exhaust the air from respective ones of the specimen chamber and the probe exchange chamber.

9. A defective product inspection apparatus for inspecting a product as a specimen, comprising:
   an electronic optical device including an electron beam irradiator;
   a movable stage for holding the specimen thereon;
   a specimen chamber for containing the stage therein;
   a probe contactable to the specimen in the specimen chamber;
   a probe holder for holding the probe thereon;
   a probe exchange chamber arranged at a position different from the electronic optical device to contain the probe holder therein; and
   a gate valve for connecting the specimen chamber and the probe exchange chamber to each other,
   wherein in the specimen chamber, a position of the stage obtained when exchanging the probe holder is closer to the probe exchange chamber with respect to the electronic optical device in comparison with a position of the stage obtained when inspecting the specimen, and
   the probe holder is movable on the stage and the stage is movable between a first position in the vicinity of the electronic optical device and a second position in the vicinity of the probe exchange chamber in the specimen chamber.

* * * * *